(12) United States Patent
Greenblatt et al.

(10) Patent No.: US 10,953,169 B2
(45) Date of Patent: Mar. 23, 2021

(54) SYSTEMS AND METHODS FOR REVERSE PRESSURE PULSE THERAPY DELIVERY

(71) Applicants: Elliot E. Greenblatt, Boston, MA (US); Jose G. Venegas, Swampscott, MA (US)

(72) Inventors: Elliot E. Greenblatt, Boston, MA (US); Jose G. Venegas, Swampscott, MA (US)

(73) Assignee: The General Hospital Corporation, Boston, MA (US)

( * ) Notice: Subject to any disclaimer, the term of this patent is extended or adjusted under 35 U.S.C. 154(b) by 1115 days.

(21) Appl. No.: 15/037,434

(22) PCT Filed: Nov. 19, 2014

(86) PCT No.: PCT/US2014/066360
§ 371 (c)(1),
(2) Date: May 18, 2016

(87) PCT Pub. No.: WO2015/077308
PCT Pub. Date: May 28, 2015

(65) Prior Publication Data
US 2016/0287819 A1    Oct. 6, 2016

Related U.S. Application Data

(60) Provisional application No. 61/907,639, filed on Nov. 22, 2013.

(51) Int. Cl.
*A61M 15/00*    (2006.01)
*A61M 16/00*    (2006.01)
(Continued)

(52) U.S. Cl.
CPC ........ *A61M 15/0091* (2013.01); *A61M 11/00* (2013.01); *A61M 15/0098* (2014.02);
(Continued)

(58) Field of Classification Search
CPC .............. A61M 16/00; A61M 16/0066; A61M 16/0078; A61M 16/1075; A61M 16/204;
(Continued)

(56) References Cited

U.S. PATENT DOCUMENTS 4,155,356 A  *  5/1979  Venegas ............... A61M 16/022
                                             128/204.23
4,481,944 A  *  11/1984  Bunnell ................ A61M 16/00
                                             128/203.17
(Continued)

FOREIGN PATENT DOCUMENTS

WO    2009/067549    5/2009
WO    2011/021117    2/2011

OTHER PUBLICATIONS

International Search Report and Written Opinion dated Feb. 19, 2015 for International Application No. PCT/US2014/066360.

*Primary Examiner* — Quang D Thanh
*Assistant Examiner* — Matthew R Moon
(74) *Attorney, Agent, or Firm* — Quarles & Brady LLP (57) ABSTRACT

A system and method for providing a therapy to a subject may include a lumen configured to be coupled to a portion of a respiration passage of the subject to receive air respired by the subject. A sensor is configured to monitor the lumen and generate a signal based on the air respired by the subject. A pressure pulse delivery system is configured to deliver a pressure pulse along the lumen to the subject and a reservoir of therapeutic agent is coupled to the lumen. A processor is configured to receive the signal from the sensor, determine, from at least the signal, an exhalation period of the subject, and based on the exhalation period, cause the pressure pulse delivery system to deliver a pressure pulse to the subject. Following the pressure pulse, the processor can cause the therapeutic agent to be delivered from the reservoir.

17 Claims, 6 Drawing Sheets

(51) Int. Cl.
*A61M 16/14* (2006.01)
*A61M 11/00* (2006.01)
*A61M 11/02* (2006.01)

(52) U.S. Cl.
CPC .... *A61M 16/0051* (2013.01); *A61M 16/0057* (2013.01); *A61M 16/0096* (2013.01); *A61M 16/14* (2013.01); *A61M 11/02* (2013.01); *A61M 16/0063* (2014.02); *A61M 2016/0015* (2013.01); *A61M 2016/0021* (2013.01); *A61M 2016/0027* (2013.01); *A61M 2202/0468* (2013.01); *A61M 2205/502* (2013.01); *A61M 2230/40* (2013.01)

(58) Field of Classification Search
CPC ........ A61M 16/208; A61M 2016/0015; A61M 2016/0018; A61M 2016/0021; A61M 2016/0027; A61M 2016/0039; A61M 2016/0042; A61M 2016/102; A61M 2205/3331; A61M 2205/3334; A61M 2205/3355; A61M 2205/3379; A61M 2205/3606; A61M 2205/3666; A61M 2205/42; A61M 2205/50; A61M 16/0003; A61M 16/0006; A61M 16/021; A61M 16/0096

See application file for complete search history.

(56) References Cited

U.S. PATENT DOCUMENTS

| | | |
|---|---|---|
| 2002/0026940 A1 | 3/2002 | Brooker et al. |
| 2008/0308101 A1* | 12/2008 | Spandorfer ........... A61M 16/08 128/203.14 |
| 2009/0314290 A1 | 12/2009 | Hickle |
| 2012/0247466 A1 | 10/2012 | Avni |
| 2015/0059750 A1* | 3/2015 | Arnott ................. A61M 16/202 128/204.21 |

* cited by examiner

SYSTEMS AND METHODS FOR REVERSE PRESSURE PULSE THERAPY DELIVERY

CROSS-REFERENCE TO RELATED APPLICATIONS

The application represents the U.S. National Stage of International Application No. PCT/US2014/066360, filed Nov. 19, 2014 which is based on, claims priority to, and incorporates herein by reference in its entirety U.S. Provisional Application Ser. No. 61/907,639, filed Nov. 22, 2013, and entitled, "REVERSE PRESSURE PULSE THERAPY DELIVERY SYSTEMS AND METHODS."

STATEMENT REGARDING FEDERALLY SPONSORED RESEARCH

This invention was made with government support under W81XWH-09-2-0001 awarded by the Department of Defense. The government has certain rights in the invention.

BACKGROUND

The present disclosure related to systems and methods for delivery of a therapy to a subject by inhalation. More particularly, the disclosure relates to systems and methods for delivery of a therapy to a subject using reverse pressure pulses.

Chronic obstructive pulmonary disease (COPD) plagues many people. In fact, emphysema alone affects 18 in every 1000 people. It is a seriously disabling and irreversible disease characterized by loss of lung parenchyma and dynamic airway collapse during exhalation. The collapse of airways, together with poor parenchymal tethering forces and loss of elastic recoil, work together to limit the flow rate from damaged portions of the lung during exhalation. When parts of the lung cannot properly deflate before the next inspiration begins, they become regions of trapped gas that minimally participate in ventilation. Though there are no known cures for emphysema, it is currently treated by supporting the breathing with anticholinergics, bronchodilators, steroid medication, supplemental oxygen, and a technique known as reverse pressure pulses (RPP), which uses high frequency positive pressure pulses during exhalation at the mouth.

Mechanistically, RPP is similar to pursed lip breathing, which is known to help some COPD patients to breath. However, instead of the steady expiratory pressure generated by pursed lips, RPP exposes the airway opening to a pulsating pressure during exhalation. So, in addition to enhancing exhaled flow through flow-limited points with very-small increases in average opening pressure, the pulses traveling along open airways may also increase gas mixing and enhance gas exchange along those airways. It has been demonstrated that RPP may systematically improve blood gases and reduce respiratory and cardiac frequencies in patients with emphysema during exercise. In addition, a reduction in hyperinflation was documented with fluoroscopy, cyanosis was reduced, and patients' self reported that ease of breathing improved. However, this treatment has been seen mainly as palliative, for temporary relief of breathlessness in patients with end stage emphysema.

Therefore, it would be desirable to have systems and methods for providing improved or new systems and methods for providing improved or additional relief to patients suffering from COPD or other respiratory ailments.

SUMMARY

The present disclosure overcomes the aforementioned drawbacks by monitoring respiration in a patient and utilizing carefully-timed RPP within the respiratory cycle to improve response of a patent, for example, to facilitate the delivery of a therapy to the patient. Thus, instead of serving as a means of temporary relief or therapy for patients with respiratory ailments such as COPD, the present disclosure uses carefully-timed RPP as part of a greater strategy for treating or delivering a therapy to a patient. That is, the present disclosure recognizes that RPP delivery may be carefully coordinated to reduce gas trapping in patients, allowing ventilation to the regions with the trapped gas. Furthermore, such carefully-coordinated RPP may, optionally, be combined with inhalation therapy delivered on a breath subsequent to the RPP to enhance delivery to those regions of the lung where the trapped gas has been expelled.

In accordance with one aspect of the present disclosure, a system is provided for delivering a therapy to a subject. The system may include a lumen configured to be coupled to a portion of a respiration passage of the subject to receive air respired by the subject and a sensor configured to monitor the lumen and generate a signal based on the air respired by the subject. The system may also include a pressure pulse delivery system configured to deliver a pressure pulse along the lumen to the subject and a supply of therapeutic agent coupled to the lumen. The system may also include a processor configured to receive the signal from the sensor and determine, from at least the signal, an exhalation period of the subject. Based on the exhalation period, the system can cause the pressure pulse delivery system to deliver a pressure pulse to the subject and, following the pressure pulse, cause the therapeutic agent to be delivered from the supply. The system may further include a user interface configured to receive a user selection of a pressure-pulse delivery strength. The processor may be further configured to control the operation of the pressure pulse delivery system to deliver a pressure-pulse based on the user selection of the pressure-pulse delivery strength. The user interface may be further configured to receive a user selection of a therapy delivery strength. The processor may be further configured to control operation of the supply to deliver a therapy based on the user selection of the therapy delivery strength.

In accordance with another aspect of the present disclosure, a method is provided for delivering a therapy to a subject. The method may include monitoring the respiration cycle of the subject, determining an exhalation for a subject based on monitoring the respiration pattern of the subject, and identifying a predetermined point in the respiration cycle relative to the exhalation. The method may also include delivering a pressure pulse to the subject at the predetermined point in the respiration cycle and, following the pressure pulse, delivering the therapy to the respiratory passage of the subject to be inhaled by the subject. The method may further include determining a delivery strength of the therapy based on the monitoring of the respiration cycle. The method may further include determining a delivery strength for the pressure pulse based on at least monitoring the respiration cycle.

In accordance with yet another aspect of the present disclosure, a system is provided for delivering a therapy to a subject. The system may include a lumen configured to be coupled to a portion of a respiration passage of the subject to receive air respirated by the subject. The system may also include a sensor configured to monitor the lumen and generate a signal based on the air respirated by the subject.

The system may also include a pressure pulse delivery system configured to deliver a pressure pulse along the lumen to the subject. The system may also include a supply of therapeutic agent coupled to the lumen. The system may also include a processor configured to receive the signal from the sensor. The system can also cause the therapeutic agent to be delivered from the supply and following delivery of the therapeutic agent, cause the pressure pulse delivery system to deliver a pressure pulse to the subject.

In accordance with another aspect of the present disclosure, a method is provided for delivering a therapy to a subject. The method may include monitoring the respiration cycle of the subject; delivering the therapy to the respiratory passage of the subject to be inhaled by the subject; and following the delivery of the therapy, delivering a pressure pulse to the subject.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

3B is a perspective view of an exhalation port and mouthpiece that may be used with the system of FIG. 2.

DETAILED DESCRIPTION

Figure 1:
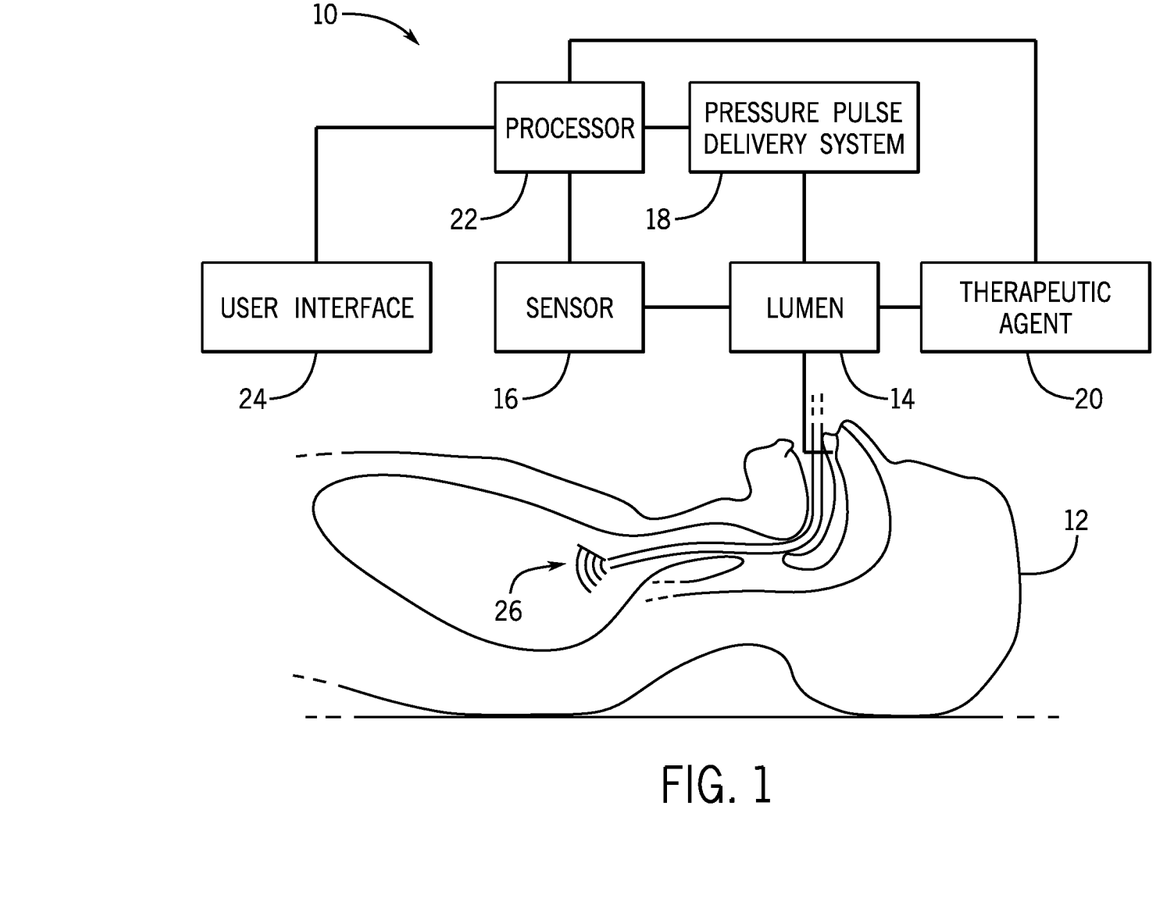
FIG. 1 is a schematic diagram of an example of a system in accordance with the present disclosure.

Referring to FIG. 1, a system 10 configured to provide a therapeutic agent 20, which may be a supply or reservoir of the therapeutic agent 20, to a subject 12 is shown. In some embodiments, the system 10 may include a lumen 14, a sensor 16, a pressure pulse delivery system 18, and a processor 22. The processor 22 may be coupled to a user interface 24, which may include user inputs, such as buttons, touch screens, and the like, as well as displays, visual and audio alarms, and the like. The lumen 14 may be coupled to a portion of the respiration passage of the subject 12, and the sensor 16 may be in communication with the lumen 14 such that sensor 16 is configured to monitor the lumen 14. The sensor 16 may also be configured to generate a signal based on the air respirated by the subject 12 into the lumen 14. The pressure pulse delivery system 18 may be configured to deliver a pressure pulse along the lumen 14 to the subject 12. The direction of the pressure pulse can be seen from the direction of the waves 26 inside the subject 12 as being directed from the pressure pulse delivery system 18, along the lumen 14, and into the subject 12. To avoid loss of the pressure pulses through the nose, the subject 12 may have a nose clip. The processor 22 may be in communication with the sensor 16 such that the processor 22 is configured to receive the signal from the sensor 16, and, based on at least that signal, determine respiration of the subject 12. The processor 22 may also be configured to cause the pressure pulse delivery system 18 to deliver a pressure pulse to the subject 12 of a predetermined magnitude. The processor 22 may also be configured to cause the pressure pulse delivery system 18 to deliver a pressure pulse to the subject 12 based on that determination of the respiration cycle. For example, as will be described, the processor 22 may be configured to determine an exhalation period and control the pressure pulse delivery system 18 to deliver a pressure pulse to the subject 12 based thereon. In addition, the processor 22 may be configured to cause the therapeutic agent 20 to be delivered to the subject 12 following the pressure pulse.

Examples of therapeutic agents 20 may include anticholinergics, short and long acting bronchodilators, steroid medication, anti-inflammatory agents, antibiotics, agents to promote pulmonary tissue regeneration, supplemental oxygen, stem cells and molecules targeting lung regeneration.

Figure 2:
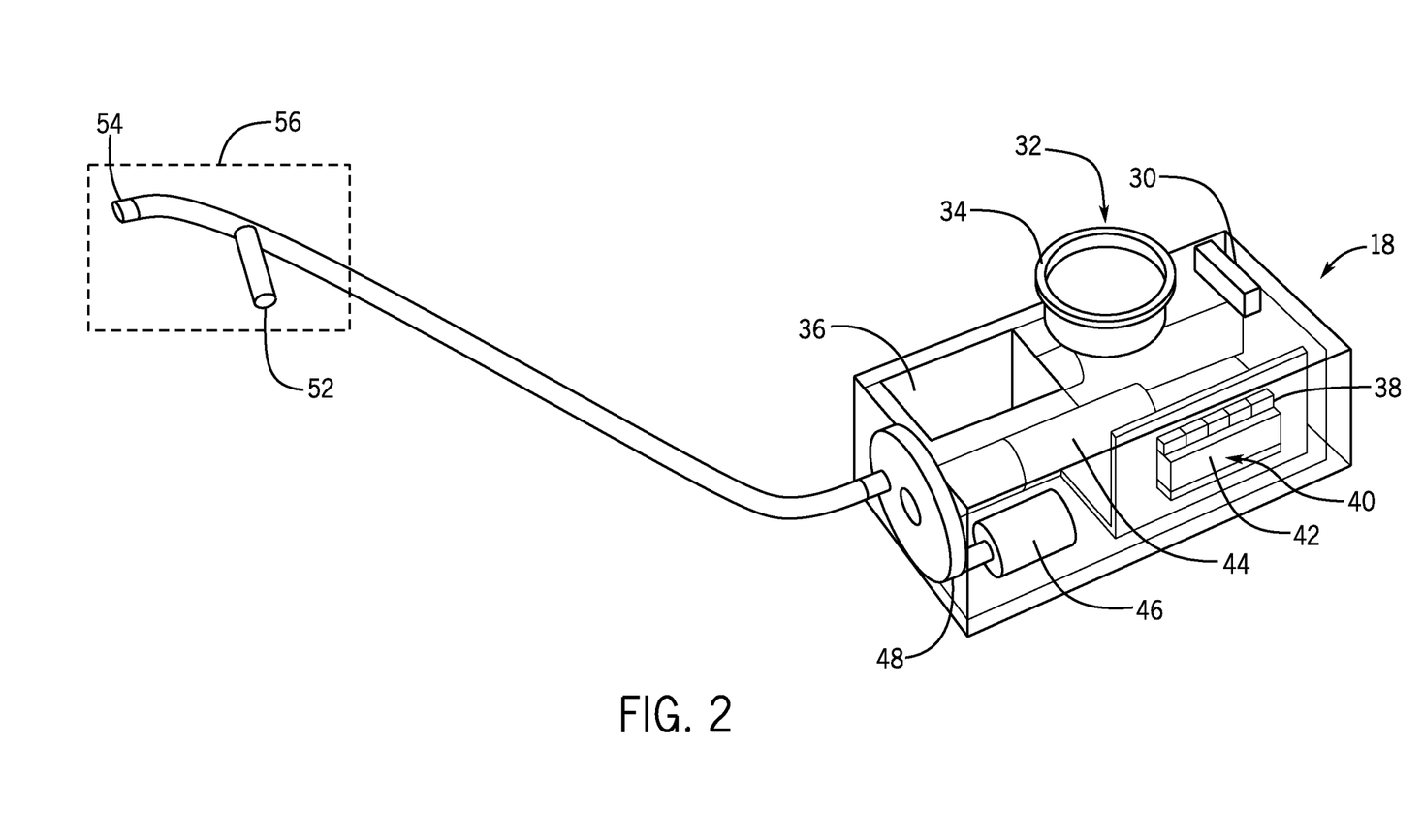
FIG. 2 is a perspective view of an example of an RPP generator system in accordance with the present disclosure.

Referring now to FIG. 2, an embodiment of a pressure pulse delivery system 18 is shown. The pressure pulse delivery system 18 may include a compressed air inlet port 30, a mini pressure regulator 32 (such as the Mcmaster 4158K72), a pressure gauge (not shown in FIG. 2), a DC motor controller 34 (such as the Maxon DEC 50-5 Controller), an air reservoir 36, control buttons 38, and a display 40, a servo controller 42 (such as the Pololu Orangutan SVU Controller), a DC motor 44 (such as the Maxon EC Powermax 22 DC Motor), a DC power adapter port (not shown in FIG. 2), a pressure transducer 46, a reduction gear 48 (such as the Maxon 14:1 Reduction Gear), a valve housing containing a valve (not shown), and a pressure sensor (not shown in FIG. 2). The system 18 includes an exhalation port 52 and a mouthpiece 54 that, collectively, form a patient interface device 56. The compressed air inlet port 30 may be configured to receive compressed air for delivery of the pressure pulses. The mini pressure regulator 32 may be configured to regulate the pressure of the compressed air based on user input entered into the pressure pulse delivery system 18 using the control buttons 38 and display 40. The pressure gauge may be configured to sense pressure of the compressed air coming into the pressure pulse delivery system 18.

The DC motor controller 42 may be configured to control the DC motor 44 based on user input entered into the pressure pulse delivery system 16 using the control buttons 38 and display 40. The air reservoir 36 may be configured to pressurized air for delivery to the subject 12. The servo controller 42 may be USB programmable and may be configured to be controlled by user input entered into the pressure pulse delivery system 16 using, for example, the control buttons 38 and display 40. The mouthpiece 54 may be in communication with the subject 12 for delivery of the pressure pulses of the pressure pulse delivery system 18 to the subject 12. The exhalation port 52 may be used to allow the outlet of exhaled air from the subject 12. The pressure sensor may be configured to measure the pressure of the delivered pressure pulse and display that pressure on the display 40.

Figure 3A:
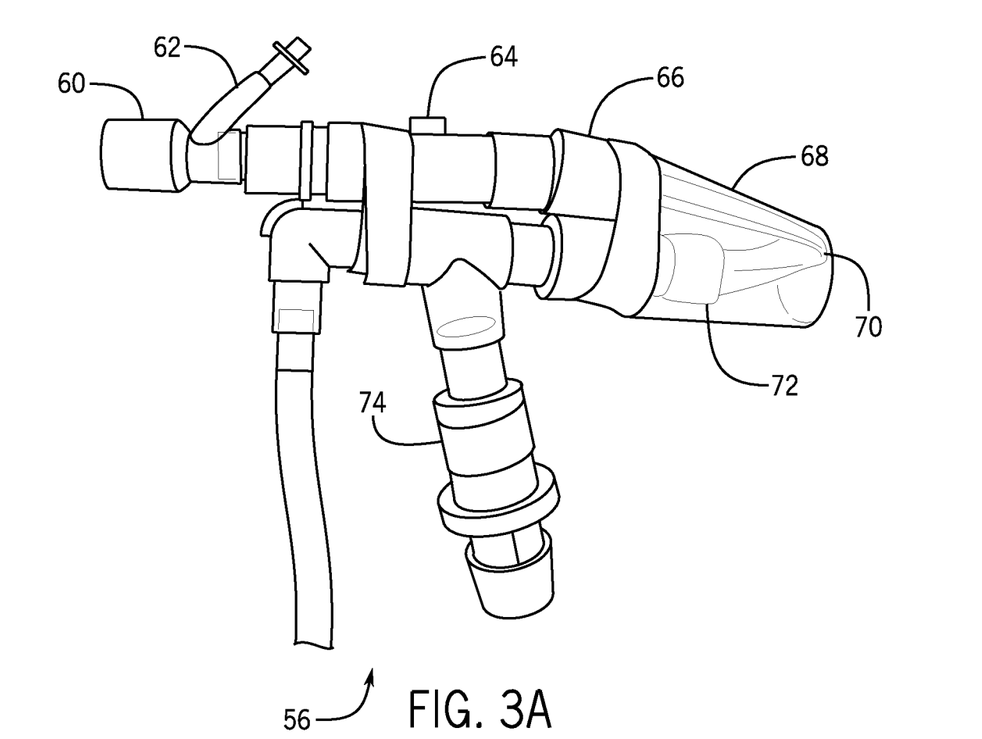
FIG. 3A is a perspective view of a exhalation port and mouthpiece that may be used with the system of FIG. 2.

Referring now to FIG. 3A, one configuration of the patient-interface device 56 (including the mouthpiece 54 and the exhalation port 52) I is shown. The patient-interface device 56 may include a mouthpiece 60 for communication between the subject 12 and the pressure pulse delivery system 18, a pressure sensor 62 just upstream from the mouthpiece 60, an exhaust port 64 upstream from the pressure sensor 62, a resistance band 66 upstream from the exhaust port 64, penrose tubing 68 upstream from the resistance band 66, a pinch point 70 in the penrose tubing 68, a volume limiter 72 upstream from the penrose tubing 68, a positive end expiratory pressure (PEEP) valve 74 upstream from the volume limiter 72, and an air supply for supplying the pressure pulses upstream from the volume limiter 72. The principle of operation of the patient-interface device 56 is that, when the pinch point 70 is closed, the penrose tubing 68 inflates with air until the expansion opens the pinch point 70. The pressure set by the PEEP valve 74 is then applied to the respiratory system of the subject 12 until the penrose tubing 68 deflates by way of the resistance band 66. At that point, the pinch point 70 seals and returns the device 56 to its initial position. When the device 56 returns to its initial position, the cycle restarts. The volume limiter 72 may be used to limit the volume of air entering the penrose tubing 68 so as not to burst the penrose tubing 68 or supply to much pressure to the subject 12. The pressure sensor 62 may be configured to measure the pressure of the exhalation of the subject 12 or the pressure of the pressure pulses. The exhaust port may be configured for allowing the outlet of exhaled air from the subject 12.

Figure 3B:
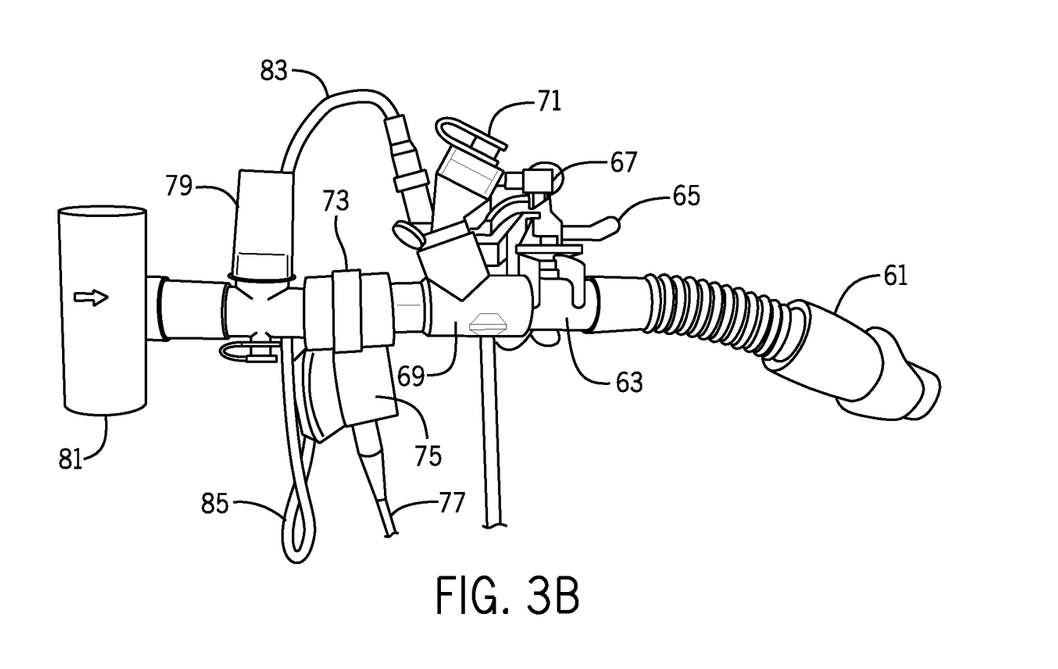

Also, FIG. 3B shows another configuration for the patient-interface device 56. In particular, the patient-interface device 56 may include a mouthpiece 61, a port 63 for measuring the pressure of the RPP pulses upstream from the mouthpiece 61, a filter 65 for protecting a pressure sensor 67 from moisture upstream from the mouthpiece 61, a nebulizer connector 69 upstream from the port 63 for directing a nebulization from a nebulizer 71 to the mouthpiece 61, a pulse injector 73 upstream from the nebulizer connector 69 for sending pulses of air to the mouthpiece 61, a fast solenoid valve 75 upstream from the pulse injector 73 for managing pressure pulses, and a regulated air compressor 77 upstream from the fast solenoid valve 75 for a pressurized air supply. The patient-interface device 56 may also include an exhalation port 79 and an inhalation port 81 both upstream from the pulse injector 73, a first data cable 83 for communicating a gated nebulizer signal, and a second data cable 85 for communicating an RPP signal. The principle of operation of the patient-interface device 56 is that the subject 12 may breathe in and out through the mouthpiece 61 using inhalation port 81 and exhalation port 79. At the same time, the second data cable 85 may communicate an RPP signal for the pulse injector 73 and fast solenoid valve 75 to deliver pressure pulses to the subject 12. In addition, the first data cable 83 may communicate a gated nebulizer signal for the nebulizer 71 to deliver a therapy to the subject 12 through the nebulizer connector 69 during inhalation. The pressure sensor 67 may be configured to measure the pressure of the pulses to the subject 12 and the start of inhalation by the subject 12 for when the nebulizer 71 should deliver the therapy.

Figure 4:
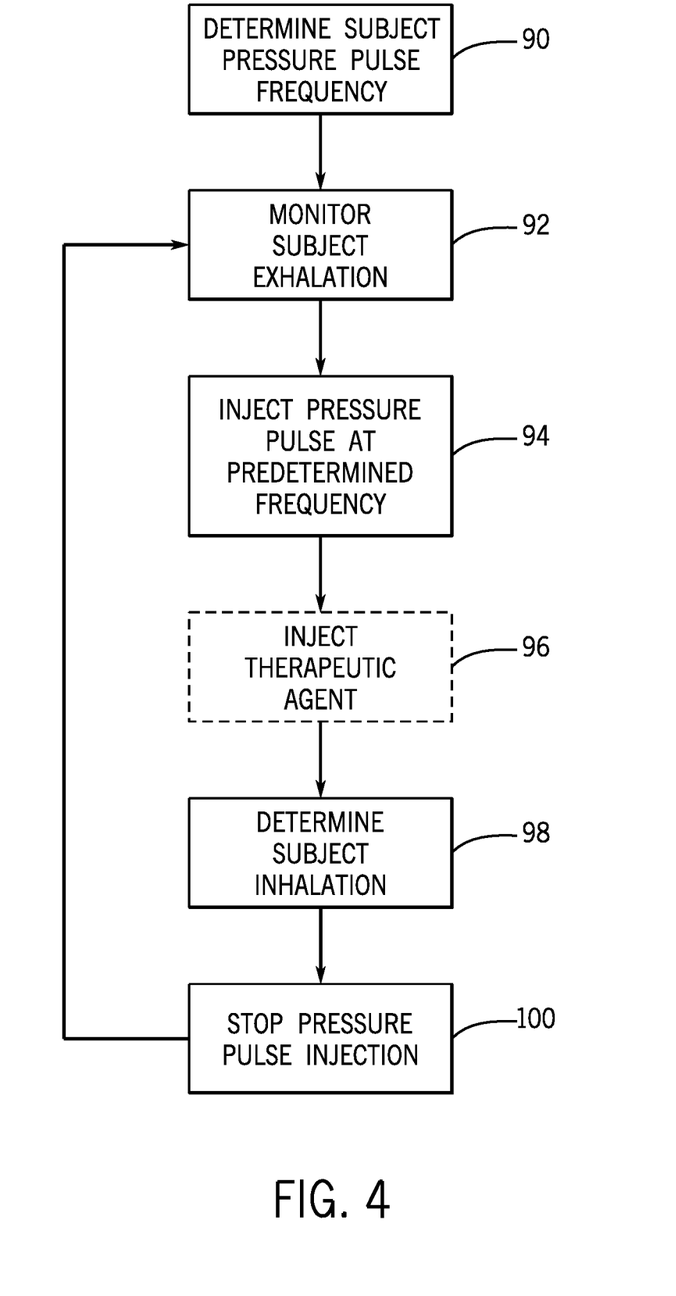
FIG. 4 is a flowchart setting forth the steps of an example of a method of operation for a system in accordance with the present disclosure.

Referring now to FIG. 4, a flowchart setting forth the steps of an example of a method for delivering a therapy to a subject is shown. The first step is to determine the pressure pulse frequency at which to deliver pressure pulses to the subject 12, as indicated in step 90. For example, it may be desirable to deliver a pressure pulse as frequently as possible for some patients, whereas for other patients, the delivery of the pressure pulse may be less frequent. It is contemplated that the frequency may be supplied by a user or clinician or may be determined by the system by monitoring the respiration of the subject. For example, a subject with an erratic or shallow respiration process may benefit from a higher frequency, whereas the converse is also possible. If not supplied by the user or clinician, monitoring of an exhalation cycle of the subject may be performed, as indicated in step 92 and the feedback used to determine the desired frequency.

Figure 5:
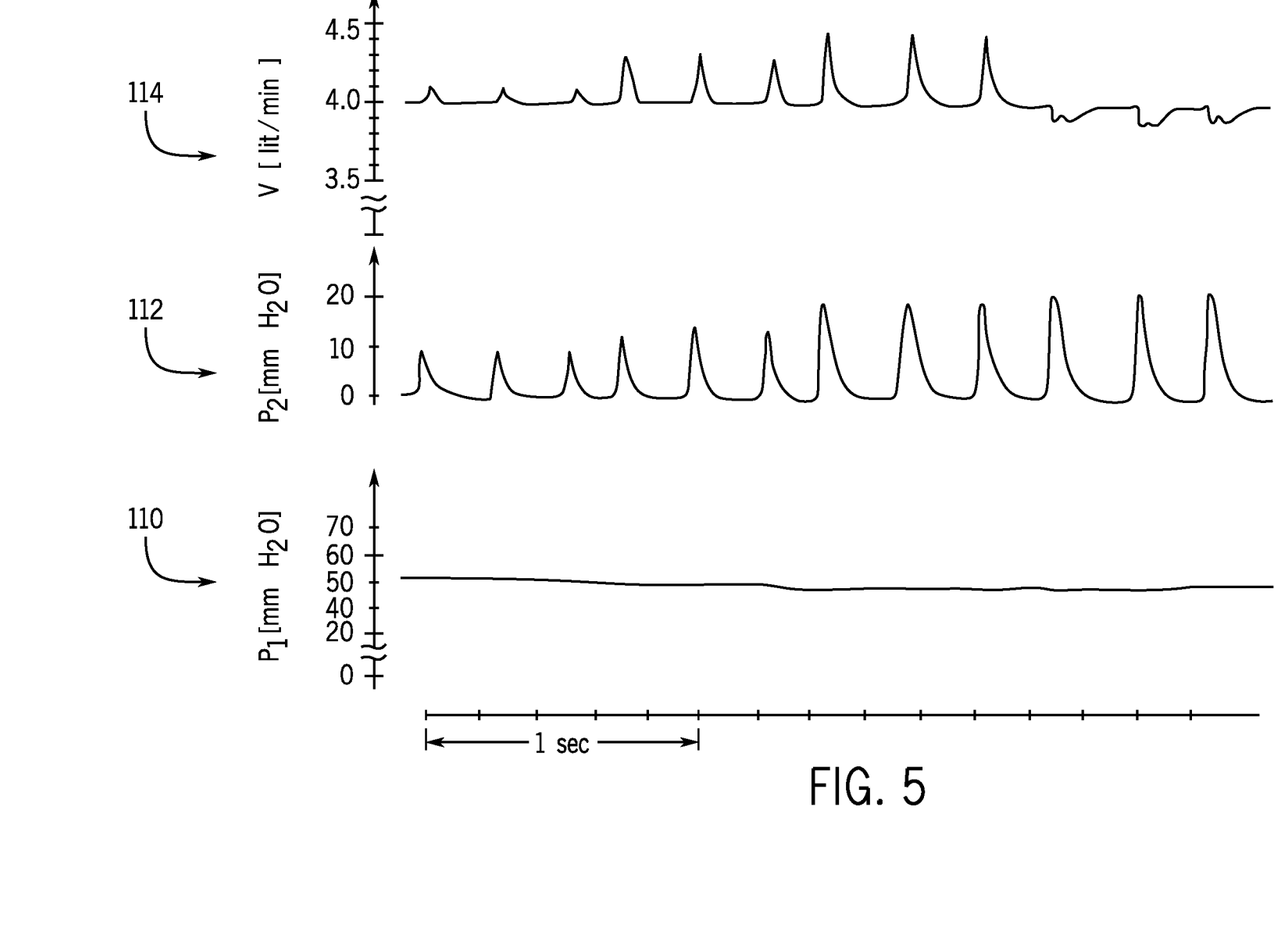
FIG. 5 is a graph illustrating the flow rate of a flow-limited starling resistor driven by a constant upstream pressure with positive pressure pulses.

Next, with respiration cycle and pressure pulse frequency determined, a pressure pulse may be injected into the subject 12, as indicated in step 94. In particular, referring to FIG. 5, a series of charts indicating how a flow rate can be temporarily increased by injecting positive pressure pulses is shown. Chart 110 plots a constant upstream pressure over time. Chart 112 plots a series of positive pressure pulses over time. Chart 114 plots a flow rate through a flow limited starling resistor with the constant upstream pressure from chart 110 and the positive pressure pulses from chart 112 applied to it over time. These charts show how flow rate can be temporarily enhanced by delivery of positive pressure pulses to the downstream end of a tube. Chart 114 shows how the flow rate temporarily increases as the pulse amplitude is increased between 10 and about 20 mmH20. Pulses greater than 20 mmH20 temporarily inhibit flow through the tube instead of enhancing it. This demonstrates that for certain tube properties, geometry, and driving pressures there may be a certain pulse train that could optimize expiratory flow.

Referring again to FIG. 4, after the injection of the pressure pulse in step 94, a therapeutic agent may be injected into the subject, as indicated in step 96. Next, as part of ongoing respiration monitoring, an inhalation of the subject 12 may be determined, as indicated in step 98. Once the inhalation is determined, the system 10 may stop injecting the pressure pulses, as indicated in step 100. The process iterates back to step 92 once the subject 12 once again begins to exhale.

Figure 6A:
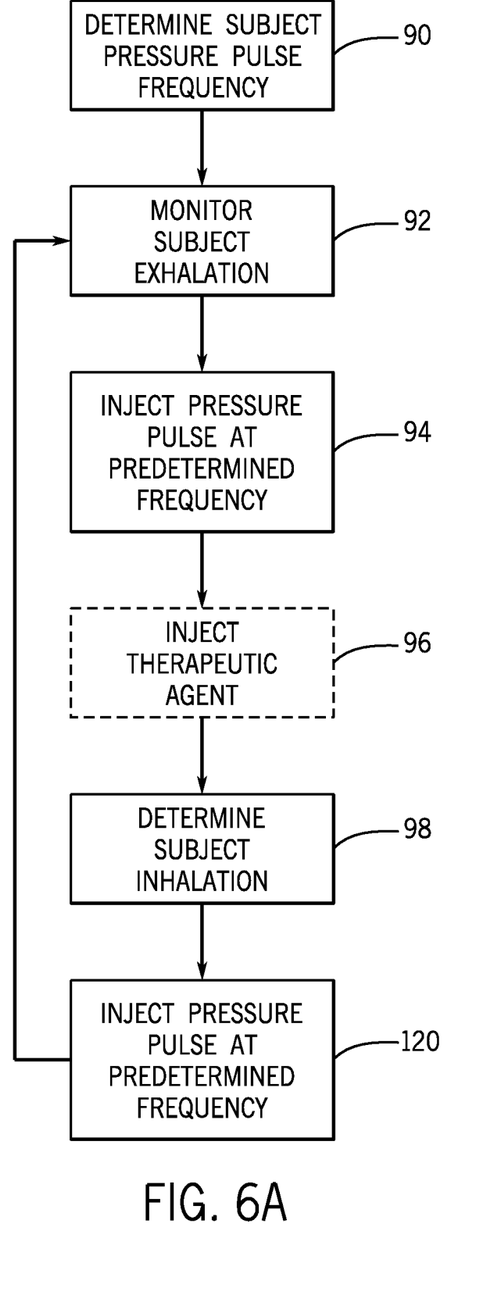
FIGS. 6A-B are flowcharts setting forth the steps of an example of a method of operation for a system in accordance with the present disclosure.
Figure 6B:
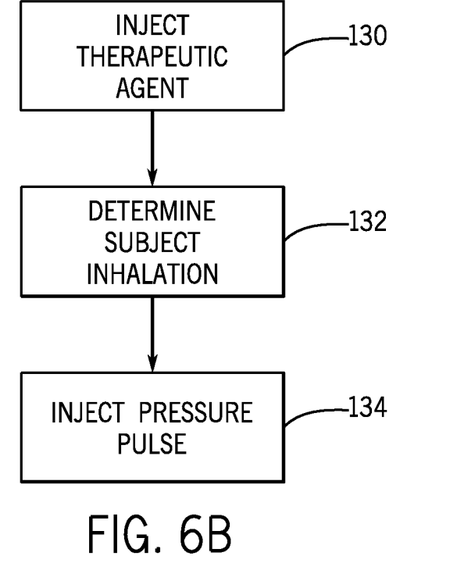

Referring now to FIGS. 6A-B, a flowchart setting forth the steps of another example of a method for delivering a therapy to a subject is shown. In particular, in FIG. 6A, this method may be used as an extension of the method from FIG. 4. Instead of stopping the injection of the pressure pulses after an inhalation in the method of FIG. 4, another pressure pulse may be injected directly after the therapy is injected or while the therapy is injected, as indicated in step 120. In this manner, the pressure pulse delivery system 18 may be used to push the therapy suspended in the respiratory system of the subject 12 onto the walls of the respiratory system of the subject 12. This method allows for higher therapy retention and allows for targeting of central deposition (by sending the pulses during the therapy delivery) or peripheral deposition (by pulsing at high lung volume after a deep inspiration of the therapy).

While the method from FIG. 6A may be used as an extension of the method from FIG. 4, the method may also be used independent of the method from FIG. 4, as shown in FIG. 6B. The therapy may be injected, as indicated in step 130. Next, an inhalation of the subject may be determined, as indicated in step 132. Finally, a pressure pulse may be sent into the respiratory system of the subject, as indicated in step 134. The pressure pulse may be injected into the respiratory system of the subject 12 during the injection of the therapy, during the inhalation, or at the maximum inhalation of the subject 12.

The present invention has been described in terms of one or more preferred embodiments, and it should be appreciated that many equivalents, alternatives, variations, and modifications, aside from those expressly stated, are possible and within the scope of the invention.

What is claimed is:

1. A system for providing a therapy to a subject, the system comprising:
   a lumen configured to be coupled to a portion of a respiration passage of the subject to receive air respirated by the subject;
   a sensor configured to monitor the lumen and generate a signal based on the air respirated by the subject;
   a pressure pulse delivery system configured to deliver a pressure pulse along the lumen to the subject;
   a supply of therapeutic agent coupled to the lumen, wherein the pressure pulse delivery system is upstream of the supply of therapeutic agent; and
   a processor configured to:
      receive the signal from the sensor;
      determine, from at least the signal, an exhalation of the subject;
      upon determining a start of the exhalation, cause the pressure pulse delivery system to deliver the pressure pulse to the subject;
      determine, from at least the signal, a start of inhalation of the subject that follows the start of the exhalation without an intervening inhalation or exhalation; and
      upon determining the start of inhalation, cause the pressure pulse delivery system to stop delivery of the pressure pulse and cause delivery of the therapeutic agent from the supply.

2. The system according to claim 1, further comprising a user interface configured to receive a user selection of a pressure-pulse delivery frequency and wherein the processor is further configured to coordinate operation of the pressure pulse delivery system based on the user selection and the exhalation.

3. The system according to claim 2, wherein the user interface is further configured to receive a user selection of a pressure-pulse delivery strength and wherein the processor is further configured to control operation of the pressure pulse delivery system to deliver the pressure pulse based on the user selection of the pressure-pulse delivery strength.

4. The system according to claim 3, wherein the user interface is further configured to receive a user selection of a therapy delivery strength and wherein the processor is further configured to control operation of the supply to deliver the therapeutic agent based on the user selection of the therapy delivery strength.

5. The system according to claim 1, wherein the processor is further configured to cause the pressure pulse delivery system to deliver a pressure pulse to the subject after the delivery of the therapeutic agent but before a subsequent exhalation.

6. A method for providing a therapy to a subject, the method including steps comprising:
   (a) providing a lumen configured to be coupled to a portion of a respiratory passage of the subject to receive air respirated by the subject, a pressure pulse delivery system configured to deliver a pressure pulse along the lumen to the subject, and a supply of therapeutic agent coupled to the lumen, wherein the pressure pulse delivery system is upstream of the supply of therapeutic agent;
   (b) monitoring a respiration cycle of the subject;
   (c) determining an exhalation of the subject based on monitoring the respiration cycle of the subject;
   (d) following determining the exhalation and before a subsequent inhalation, delivering, from the pressure pulse delivery system, the pressure pulse to the subject;
   (e) determining an inhalation of the subject that is directly subsequent to the exhalation in the respiration cycle of the subject based on monitoring the respiration cycle of the subject; and
   (f) following determining the inhalation that is directly subsequent to the exhalation, pausing delivery of the pressure pulse from the pressure pulse delivery system and delivering, from the supply of therapeutic agent, the therapeutic agent to the respiratory passage of the subject to be inhaled by the subject without resuming delivery of the pressure pulse during the therapeutic agent delivery.

7. The method according to claim 6, wherein step (b) further comprises determining a delivery frequency for the pressure pulse based on at least monitoring the respiration cycle.

8. The method according to claim 6, wherein step (b) further comprises determining a delivery strength of the therapeutic agent based on at least monitoring the respiration cycle.

9. The method according to claim 6, wherein step (b) further comprises determining a delivery strength for the pressure pulse based on at least monitoring the respiration cycle.

10. The method according to claim 6, further comprising (g) following the delivery of the therapeutic agent but before a subsequent exhalation, delivering, from the pressure pulse delivery system, the pressure pulse to the subject.

11. A system for providing a therapy to a subject, the system comprising:
    a lumen configured to be coupled to a portion of a respiration passage of the subject to receive air respirated by the subject;
    a sensor configured to monitor the lumen and generate a signal based on the air respirated by the subject;
    a pressure pulse delivery system configured to deliver a pressure pulse along the lumen to the subject;
    a supply of therapeutic agent coupled to the lumen, wherein the pressure pulse delivery system is upstream of the supply of therapeutic agent; and
    a processor configured to:
       receive the signal from the sensor and determine an inhalation of the subject and an exhalation of the subject;
       cause the therapeutic agent to be delivered from the supply only when the subject is inhaling; and
       following delivery of the therapeutic agent and only when the subject is exhaling, cause the pressure pulse delivery system to deliver the pressure pulse to the subject.

12. The system according to claim 11, wherein the processor is further configured to determine, from at least the signal, the inhalation of the subject and cause the therapeutic agent to be delivered from the supply during the inhalation.

13. The system according to claim 12, wherein the processor is further configured to determine, from at least the signal, the exhalation of the subject and cause the pressure pulse delivery system to deliver the pressure pulse to the subject based on the exhalation.

14. The system according to claim 13, wherein the processor is further configured to cause the therapeutic agent to be delivered during the inhalation after pausing the delivery of the pressure pulse.

15. A method for providing a therapy to a subject, the method including steps comprising:
    (a) providing a lumen configured to be coupled to a portion of a respiratory passage of the subject to receive air respirated by the subject, a pressure pulse delivery system configured to deliver a pressure pulse along the lumen to the subject, and a supply of therapeutic agent coupled to the lumen, wherein the pressure pulse delivery system is upstream of the supply of therapeutic agent;

(b) monitoring a respiration cycle of the subject;

(c) delivering, from the supply of therapeutic agent, the therapeutic agent to the respiratory passage of the subject to be inhaled by the subject; and (d) following the delivery of the therapeutic agent and only during exhalation, delivering, from the pressure pulse delivery system, the pressure pulse to the subject.

16. The method according to claim 15, wherein step (b) further comprises:

determining the exhalation of the subject based on monitoring the respiration cycle of the subject; and following determining the exhalation, delivering the pressure pulse to the subject.

17. The method according to claim 16, wherein step (c) further comprises:

determining an inhalation of the subject based on monitoring the respiration cycle of the subject; and following determining the inhalation, pausing the delivery of the pressure pulse during the inhalation.

* * * * *